US010703771B2

(12) United States Patent
Franci et al.

(10) Patent No.: US 10,703,771 B2
(45) Date of Patent: *Jul. 7, 2020

(54) FLUORIDE TRAPPING ARRANGEMENT (71) Applicant: GE Healthcare Limited, Buckinghamshire (GB)

(72) Inventors: Xavier Franci, Loncin (BE); Steve Lignon, Loncin (BE); Audrey Marie Lange, Loncin (BE); Nicolas Verbrugge, Loncin (BE)

(73) Assignee: GE HEALTHCARE LIMITED, Buckinghamshire (GB)

( * ) Notice: Subject to any disclaimer, the term of this patent is extended or adjusted under 35 U.S.C. 154(b) by 409 days.

This patent is subject to a terminal disclaimer.

(21) Appl. No.: 15/526,139

(22) PCT Filed: Nov. 12, 2015

(86) PCT No.: PCT/EP2015/076475
§ 371 (c)(1),
(2) Date: May 11, 2017

(87) PCT Pub. No.: WO2016/075259
PCT Pub. Date: May 19, 2016

(65) Prior Publication Data
US 2017/0320901 A1 Nov. 9, 2017

(30) Foreign Application Priority Data

Nov. 12, 2004 (GB) .................................. 1420094.3

(51) Int. Cl.
C07B 59/00 (2006.01)
C07H 5/02 (2006.01)
(Continued)

(52) U.S. Cl.
CPC ........... *C07H 5/02* (2013.01); *A61K 51/0497* (2013.01); *B01D 15/14* (2013.01);
(Continued)

(58) Field of Classification Search
CPC ...... B01L 19/004; B01L 19/08; B01L 19/081; B01J 2219/00927; B01J 19/004;
(Continued)

(56) References Cited

U.S. PATENT DOCUMENTS

2007/0036258 A1 2/2007 Ito et al.
2011/0305618 A1* 12/2011 Graham ................ A61K 51/04
423/249
(Continued)

FOREIGN PATENT DOCUMENTS

EP 0798307 A1 10/1997
JP 2007319254 A 12/2007
(Continued)

OTHER PUBLICATIONS

International Search Report and the Written Opinion of the International Searching Authority, or the Declaration from International Appl. No. PCT/EP2015/076475, dated Feb. 19, 2016.
(Continued)

*Primary Examiner* — Jill A Warden
*Assistant Examiner* — Dwayne K Handy
(74) *Attorney, Agent, or Firm* — Culhane Meadows PLLC; Jeff B. Vockrodt (57) ABSTRACT

The present invention provides a new chemical process, a new cassette configuration, and new software for the automated production of multiple batches of an [$^{18}$F]labelled compound on a single cassette. The invention allows one synthesizer in one hot cell to produce sequentially a plurality of batches of [$^{18}$F]-labelled PET tracer in the same day. In particular, the present invention provides a novel arrange-
(Continued)

ment useful for the trapping of [$^{18}$F]fluoride and recovery of [$^{18}$O]water.

20 Claims, 7 Drawing Sheets

(51) Int. Cl.
| | |
|---|---|
| *B01J 41/09* | (2017.01) |
| *A61K 51/04* | (2006.01) |
| *B01D 15/14* | (2006.01) |
| *B01D 15/18* | (2006.01) |
| *B01D 15/36* | (2006.01) |
| *B01D 15/42* | (2006.01) |
| *B01J 41/04* | (2017.01) |
| *B01J 41/20* | (2006.01) |
| *B01J 47/022* | (2017.01) |
| *C07H 1/06* | (2006.01) |

(52) U.S. Cl.
CPC ....... *B01D 15/1885* (2013.01); *B01D 15/363* (2013.01); *B01D 15/424* (2013.01); *B01J 41/04* (2013.01); *B01J 41/09* (2017.01); *B01J 41/20* (2013.01); *B01J 47/022* (2013.01); *C07B 59/00* (2013.01); *C07H 1/06* (2013.01); *C07B 2200/05* (2013.01)

(58) Field of Classification Search
CPC ......... B01J 19/08; B01J 19/081; C07B 59/00; C07B 59/002; C07B 59/005; C07B 2200/05
See application file for complete search history.

(56) References Cited

U.S. PATENT DOCUMENTS

| | | | |
|---|---|---|---|
| 2012/0108858 A1* | 5/2012 | Kiselev | A61K 51/0491 570/123 |
| 2012/0283490 A1 | 11/2012 | Gangadharmath et al. | |
| 2013/0144052 A1* | 6/2013 | Mueller | B01J 19/0093 536/122 |

FOREIGN PATENT DOCUMENTS

| | | |
|---|---|---|
| JP | 2014535041 A | 12/2014 |
| JP | 2015501418 A | 1/2015 |
| JP | 2017503752 A | 2/2017 |
| WO | 2013/048813 A1 | 4/2013 |
| WO | 2013/049608 A2 | 4/2013 |
| WO | 2015/071288 A1 | 5/2015 |

OTHER PUBLICATIONS

Great Britain Search Report from GB Appl. No. GB1420094.3, dated Mar. 10, 2015.
Japan Notice of Reasons for Rejection corresponding to Japanese Application No. 2017-52280, dated Jul. 16, 2019.

* cited by examiner

FLUORIDE TRAPPING ARRANGEMENT

TECHNICAL FIELD OF THE INVENTION

The present invention concerns devices and methods for the automated synthesis of [$^{18}$F]-labelled compounds, in particular those suitable for use as in vivo imaging agents for positron emission tomography (PET). The focus of the present invention is for the automated synthesis of more than one batch of an [$^{18}$F]-labelled compound using just one disposable cassette and in particular a novel system for trapping and elution of [$^{18}$F]fluoride.

DESCRIPTION OF RELATED ART

Radiolabelled compounds for use as in vivo imaging agents are currently typically prepared by means of an automated synthesis apparatus (alternatively "radiosynthesizer"). Such automated synthesis apparatuses are commercially available from a range of suppliers, including: GE Healthcare; CTI Inc.; Ion Beam Applications S.A. (Chemin du Cyclotron 3, B-1348 Louvain-La-Neuve, Belgium); Raytest (Germany) and Bioscan (USA). The radiochemistry takes place in a "cassette" or "cartridge" designed to fit removably and interchangeably onto the apparatus, in such a way that mechanical movement of moving parts of the apparatus controls the operation of the cassette. Suitable cassettes may be provided as a kit of parts that is assembled onto the apparatus in a number of steps, or may be provided as a single piece that is attached in a single step, thereby reducing the risk of human error. The single piece arrangement is generally a disposable single use cassette which comprises all the reagents, reaction vessels and apparatus necessary to carry out the preparation of a given batch of radiopharmaceutical.

Figure 1:
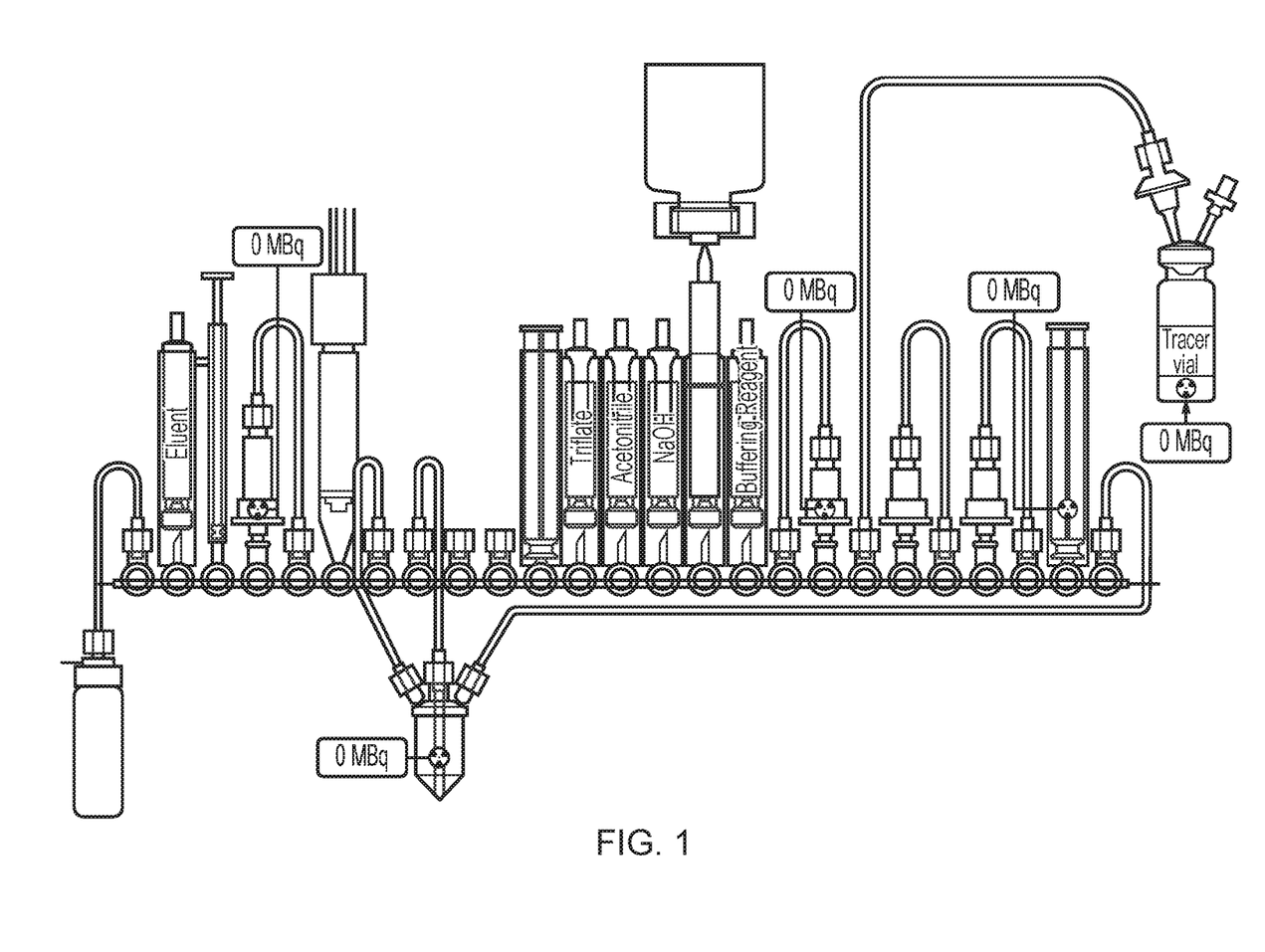
FIG. 1 and FIG. 2 illustrate examples of known cassettes for the production of one batch per cassette of an $^{18}$F-labelled compound.
Figure 2:
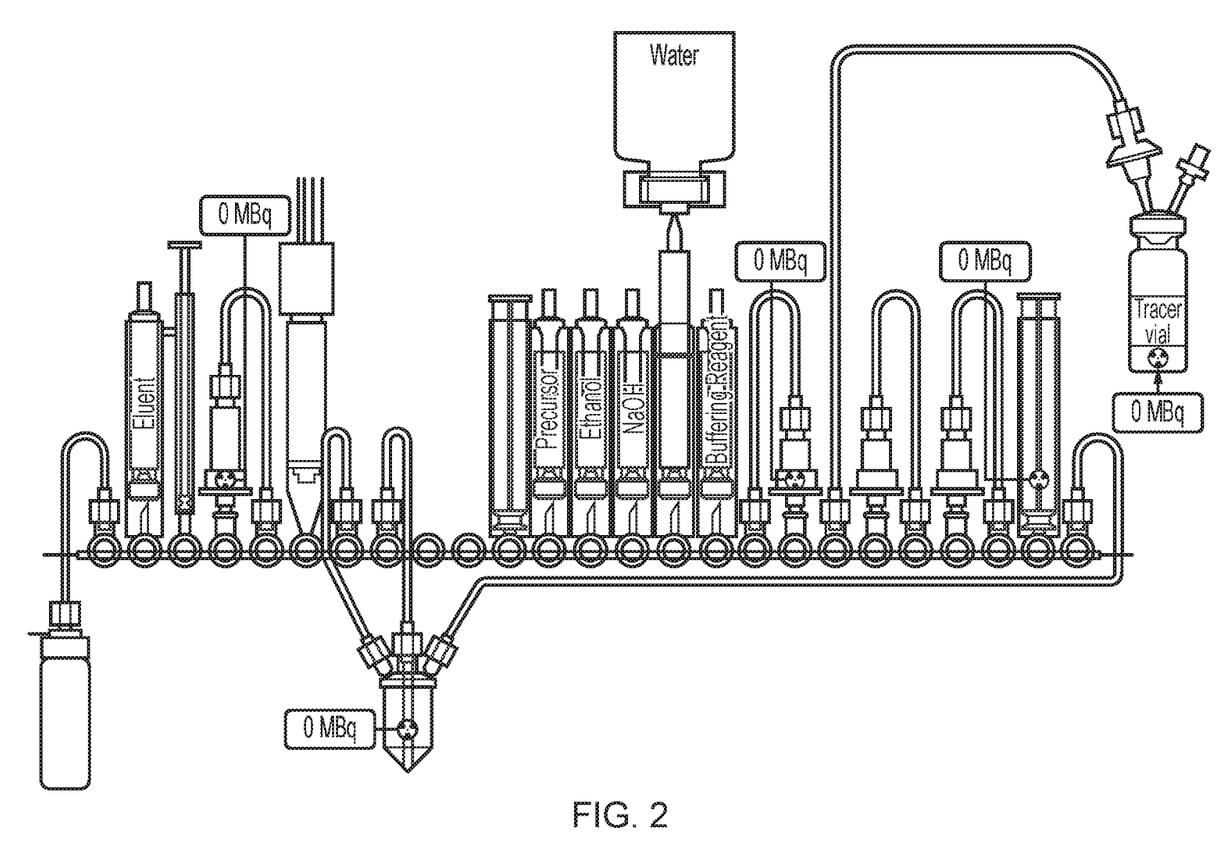

The commercially-available GE Healthcare FASTlab™ cassette is an example of a disposable single piece type of cassette pre-loaded with reagents comprising a linear array of valves, each linked to a port where reagents or vials can be attached. Each valve has a male-female joint which interfaces with a corresponding moving arm of the automated synthesis apparatus. External rotation of the arm thus controls the opening or closing of the valve when the cassette is attached to the apparatus. Additional moving parts of the apparatus are designed to clip onto syringe plunger tips, and thus raise or depress syringe barrels. The FASTlab™ cassette has 25 identical 3-way valves in a linear array, examples of which are shown in FIGS. 1 and 2. FIG. 1 is a schematic drawing of the commercially-available FDG Phosphate FASTlab™ cassette, and FIG. 2 the commercially-available FDG Citrate FASTlab™ cassette.

Synthesis of [$^{18}$F]fluorodeoxyglucose ([$^{18}$F]FDG) on the cassettes of FIGS. 1 and 2 is carried out by nucleophilic fluorination using [$^{18}$F]fluoride produced by a $^{18}$O(p,n)$^{18}$F$^-$ reaction. The $^{18}$F$^-$ so-produced enters the cassette at position 6 (i.e. 6$^{th}$ valve from the left) and travels to a QMA (quaternary methyl ammonium anion exchange) solid phase extraction (SPE) column placed at position 4 via tubing at position 5. The $^{18}$F$^-$ is retained by an ion-exchange reaction and the$^{18}$O-water is allowed to flow through the common pathway of the cassette to be recovered at position 1. $^{18}$F$^-$ retained on the QMA is then eluted with an eluent solution (acetonitrile solution of Kryptofix™ 222 and potassium carbonate at position 2, marked "Eluent") withdrawn in the syringe at position 3 and into the reaction vessel (illustrated to the bottom of the figure and connected by three tubings, one leading to each of positions 7, 8 and 25). Water is evaporated and mannose triflate precursor (from position 12, marked "Precursor") is added to the reaction vessel. Then the $^{18}$F-labelled mannose triflate ($^{18}$F-fluoro-tetraacetyl-glucose, FTAG) is trapped and so separated from $^{18}$F fluorides on an environmental tC18 SPE column at position 18 via tubing at position 17 to undergo hydrolysis with NaOH (from the vial at position 14, marked "NaOH")) to remove acetyl protecting groups. The resulting hydrolyzed basic solution is then neutralized in the syringe placed at position 24 with phosphoric acid in the case of phosphate configuration (FIG. 1) or hydrochloric acid present in a citrate buffer in the case of citrate configuration (FIG. 2). Potential residual $^{18}$F fluoride removal takes place on an alumina SPE column at position 20 via tubing at position 21 and removal of weakly hydrophilic impurities on an HLB SPE column (for the phosphate cassette of FIG. 1) or a tC18 SPE column (for the citrate cassette of FIG. 2) at position 22 via tubing at position 23. The final purified solution of $^{18}$F-FDG is transferred to a collection vial via long tubing connected at position 19.

2 positions on the FASTlab™ cassette are free in the case of each of the known [$^{18}$F]FDG cassettes illustrated in FIGS. 1 and 2, i.e. positions 9 and 10. Caps are placed on the valves at these positions.

A typical [$^{18}$F]FDG production site produces a minimum of 2 batches of [$^{18}$F]FDG a day. However, because of the residual activity on the FASTlab™ cassette, transfer line and the shadow from the waste bottle after completion of a batch, it is impossible for safety reasons to carry out back to back runs of the above-described process on the same apparatus. Furthermore, it is only possible to fit one FASTlab™ apparatus in a hot cell. To produce a second batch of [$^{18}$F]FDG on the same day using this process, it is necessary to have a second apparatus in a second hot cell.

It would therefore be desirable to have a means to produce more than one batch of [$^{18}$F]FDG using the FASTlab™ on the same day and in only one hot cell. For both of the above-described commercially-available FASTlab™ [$^{18}$F] FDG cassettes, 23 of the total 25 positions are used. With only 2 positions to spare, it is not possible to fit all the duplicate components for a second batch onto the same cassette.

Recycling the QMA column to use in a second batch presents a particular challenge because a salt solution is required for cleaning. In order to make this possible, it would be necessary to connect an external vial with the salt solution, thereby eliminating the "easy to plug" advantage of the FASTlab™ cassette. Furthermore, a salt solution is undesirable because it can contaminate the rest of the manifold as the salt solution must be withdrawn using a syringe and then passed through the cassette and collected to the waste at the other side of the cassette. The other solution is that two QMA columns are required to trap two different batches of incoming activity by using the same cassette.

Figure 3:
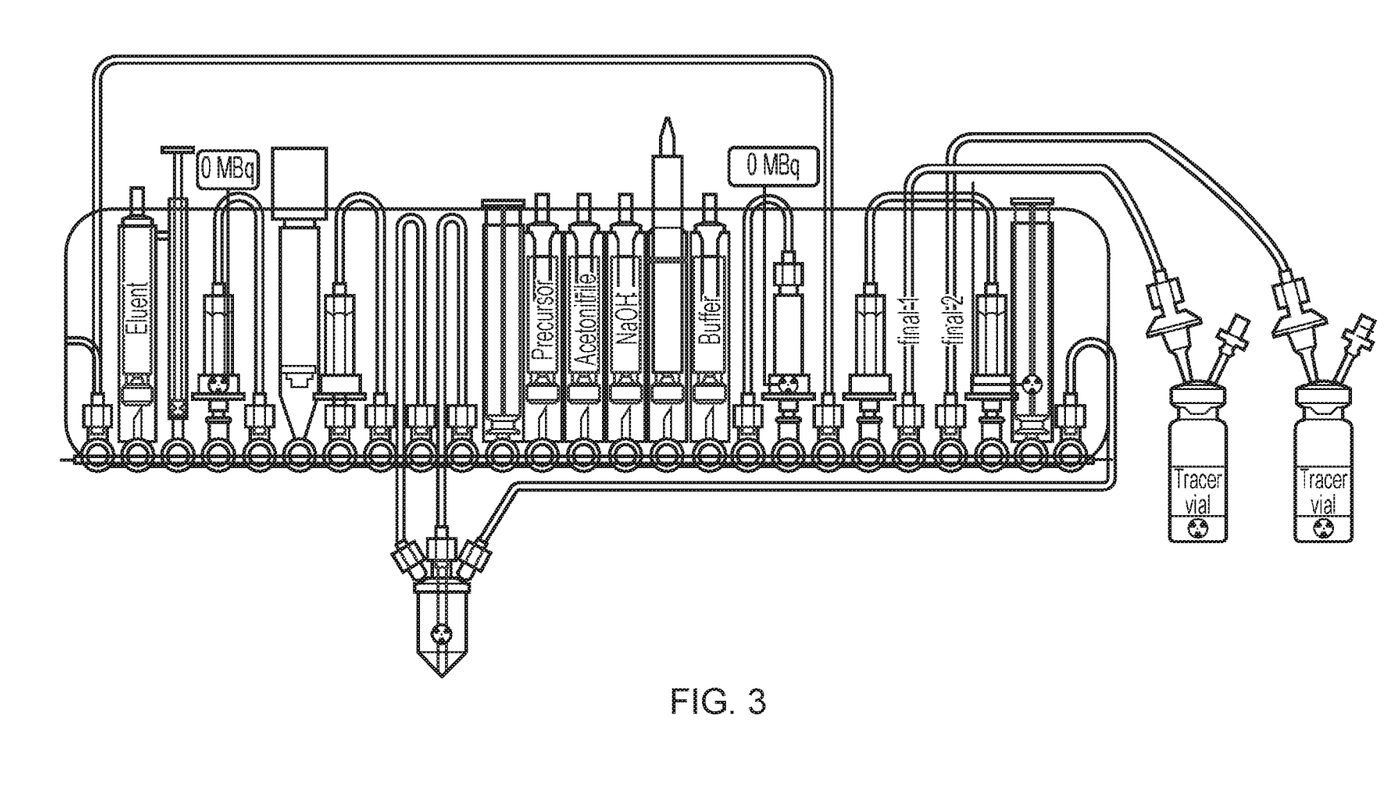
FIG. 3 illustrates an exemplary cassette described in WO2015071288.
Figure 4:
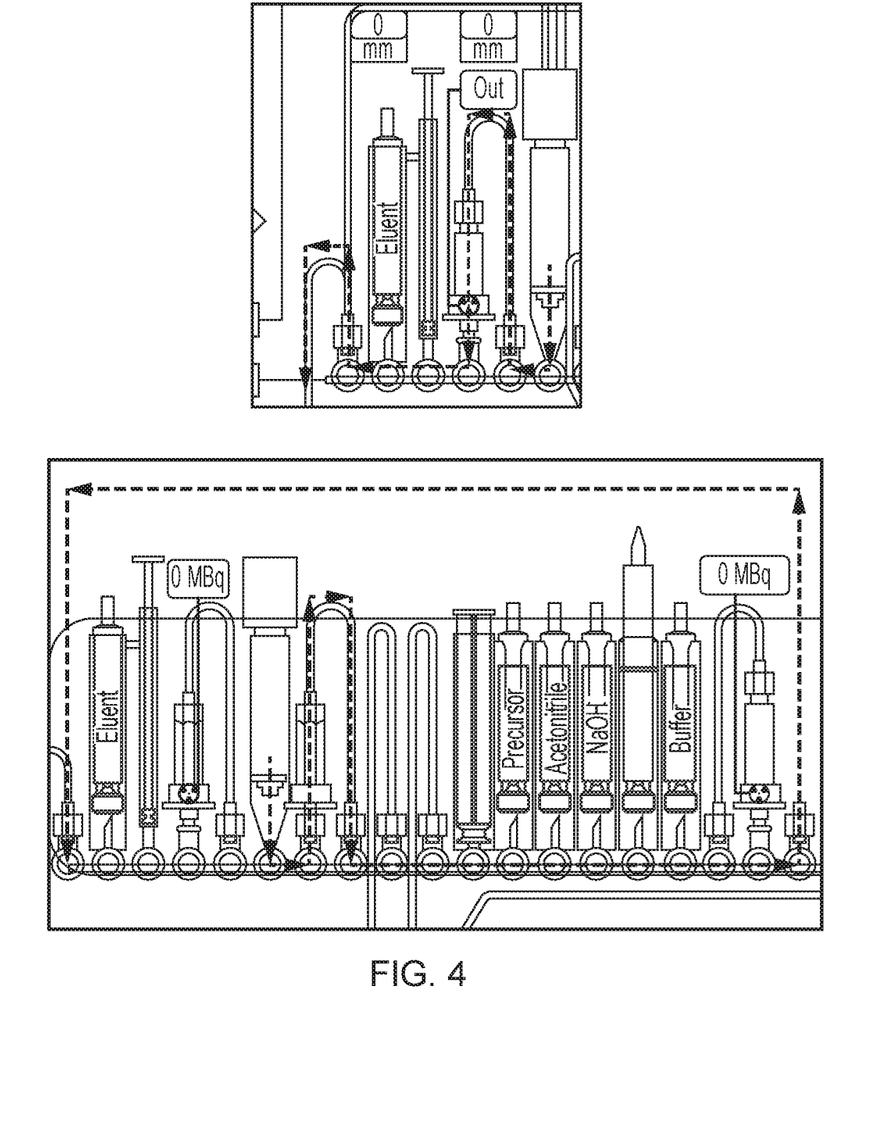
FIG. 4 illustrates the enriched water recycling pathways for the first (top) and second (bottom) batches for an exemplary cassette configuration described in WO2015071288.

WO2015071288 describes a FASTlab™ cassette for the synthesis of two batches of [$^{18}$F]FDG. FIG. 3 illustrates this single-use cassette and shows the QMA for the first [$^{18}$F] fluoride trapping at position 4 (i.e. the 4$^{th}$ valve from the left) linked to tubing connected at position 5, and the QMA for the second [$^{18}$F]fluoride trapping is at position 7 linked to tubing connected at position 8. Seven positions on the cassette are engaged in total for trapping [$^{18}$F]fluoride and recovery of enriched water, i.e. position 1 with the connection to the enriched water vial, position 6 for the [$^{18}$F] fluoride inlet, positions 4 and 5 for the first QMA and its tubing, respectively, positions 7 and 8 for the second QMA and its tubing, respectively, and position 19 for recovery of enriched water from the second batch. The enriched water recycling pathways for the first (top) and second (bottom) batches of [$^{18}$F]-fluoride are illustrated in FIG. 4. For the first batch, an aqueous solution from the nuclear reaction $^{18}$O (p,n)$^{18}$F enters the system at position 6 and passes through the first QMA at position 4 via the tubing at position 5 so that [$^{18}$F]fluoride is retained on the QMA and [$^{18}$O]-water is sent to the recovery vial via the tubing at position 1. For the second batch, the route is from position 6 to the QMA at position 7, and then to the [$^{18}$O]-water recovery vial via tubing at position 8 to the tubing at position 19 and from there to position 1 and the [$^{18}$O]-water recovery vial. So, in this cassette configuration described in WO2015071288, enriched water recovery is on the left side for the first batch and on the right side for the second batch. Quite good yields are observed for each [$^{18}$F]FDG batch using this single-use cassette and there is quite good trapping and elution of the incoming activity. However, the present inventors have found problems with this configuration; firstly contamination of the manifold with enriched water is possible because of the pathway taken for enriched water recovery to the right of the manifold for the second batch. This is a risk for the second labelling reaction. Also, as a consequence of using up seven positions for the QMA arrangement there are limited options for placement of the other components. In particular, the Oasis HLB purification column is directly connected to the alumina column so that there is no way to properly clean the Oasis HLB after the first batch because of the risk of contaminating the alumina column with organic solvent. As a result, there is a risk that non-negligible amounts of Kryptofix 2.2.2 will be present in the final product from the second batch.

It would therefore be desirable to have an improved arrangement of the FASTlab™ cassette for carrying out two [$^{18}$F]FDG runs.

SUMMARY OF THE INVENTION

In one aspect the present invention provides a system (1) for trapping [$^{18}$F]fluoride and recovering [$^{18}$O]water comprising the following components each having a first end (3a, 4a, 5a, 6a, 7a, 8a) and a respective second end (3b, 4b, 5b, 6b, 7b, 8b):
(i) a first anion exchange column (3);
(ii) a first length of tubing (4) fluidly connected at its second end to the second end of said first anion exchange column (3);
(iii) a second anion exchange column (5);
(iv) a second length of tubing (6) fluidly connected at its second end to the second end of said second anion exchange column (5);
(v) a [$^{18}$F]fluoride inlet (7); and,
(vi) a [$^{18}$O]water recovery vial (8);
wherein each first end (3a, 4a, 5a, 6a, 7a, 8a) is fluidly connected to a common pathway (2) via a valve (3c, 4c, 5c, 6c, 7c, 8c) having three ports and means to put any two of the three associated ports in fluid communication with each other while fluidly isolating the third port;
characterised in that:
said first end (4a) of said first length of tubing (4) is fluidly connected to said common pathway (2) at a point in between said second anion exchange column (5) and said [$^{18}$F]fluoride inlet (7); and,
said first end (6a) of said second length of tubing (6) is fluidly connected to said common pathway (2) at a point in between said first anion exchange column (4) and said [$^{18}$F]fluoride inlet (7).

In another aspect the present invention provides a single-use cassette (10) for the production of two consecutive batches of an [$^{18}$F]-labelled radiotracer wherein said cassette (10) comprises:
(a) the system (11) for trapping [$^{18}$F]fluoride and recovering [$^{18}$O]water as defined herein;
(b) a reaction vessel (19) and means (19a) for cleaning said reaction vessel;
(c) a vial (20) containing sufficient eluent for said two consecutive batches;
(d) a vial (21) containing sufficient precursor compound for said two consecutive batches;
(e) reagent vials (22, 23, 24, 25) each containing a particular reagent in sufficient quantity for said two consecutive batches;
(f) first (26) and second (27) reversed-phase SPE columns and respective means (26a, 27a) for cleaning said SPE columns; and,
(g) first (28) and second (29) normal-phase SPE columns, each fluidly connected to a respective product collection vial (30, 31).

In a further aspect the present invention provides a method for trapping [$^{18}$F]fluoride and recovering [$^{18}$O]water for the synthesis of two consecutive batches of [$^{18}$F]-fluoride on a single cassette wherein said method comprises the following steps in sequence:
(I) providing a system (1) for trapping [$^{18}$F]fluoride and recovering [$^{18}$O]water as defined herein;
(II) setting the valves (3c, 4c, 7c and 8c) to create a first flowpath (F1) from the [$^{18}$F]fluoride inlet (7) to the first length of tubing (4) to the first anion exchange column (3) and to the [$^{18}$O]water recovery vial (8) wherein the remaining valves (5c, 6c) are closed;
(III) sending a first aliquot of an aqueous solution obtained from the nuclear reaction $^{18}$O(p,n)$^{18}$F through said first flowpath (F1);
(IV) setting the valves (5c, 6c, 7c and 8c) to create a second flowpath (F2) from the [$^{18}$F]fluoride inlet (7) to the second length of tubing (6) to the second anion exchange column (8) and to the [$^{18}$O]water recovery vial (8) wherein the remaining valves (3c, 4c) are closed;
(V) sending a second aliquot of an aqueous solution obtained from the nuclear reaction $^{18}$O(p,n)$^{18}$F through said second flowpath (F2).

In a yet further aspect the present invention provides a method for the synthesis of two consecutive batches of an [$^{18}$F]-labelled compound on a single cassette wherein said method comprises the following steps in sequence:
(A) carrying out steps (I)-(III) of the method for trapping [$^{18}$F]fluoride and recovering [$^{18}$O]water as defined herein;
(B) eluting [$^{18}$F]fluoride trapped on said first anion exchange column (3) into a reaction vessel on said cassette wherein the reaction vessel contains a first aliquot of a precursor compound;
(C) optionally carrying out post-labelling deprotection and/or purification steps on said [$^{18}$F]-labelled product obtained in step (B) by means of one or more solid-phase extraction (SPE) cartridges on said cassette;
(D) carrying out steps (IV) and (V) of the method for trapping [$^{18}$F]fluoride and recovering [$^{18}$O]water as defined herein;
(E) eluting [$^{18}$F]fluoride trapped on said second anion exchange column (8) into a reaction vessel on said cassette wherein the reaction vessel contains a second aliquot of a precursor compound;

(F) optionally carrying out post-labelling deprotection and/or purification steps on said [$^{18}$F]-labelled product obtained in step (E) by means of one or more solid-phase extraction (SPE) cartridges on said cassette.

In another aspect the present invention provides a non-transitory storage medium comprising computer readable program code, wherein execution of the computer readable program code causes a processor to carry out the steps of the method of the invention as defined hereinabove.

The present invention permits good trapping and elution of two batches of incoming [$^{18}$F]fluoride activity, and good yields for the production of two batches of [$^{18}$F]-labelled compound. Using the system of the present invention two batches of [$^{18}$F]-fluoride can be trapped and [$^{18}$O]water recovered using fewer positions than for previous systems, thereby making a position on the cassette available for the placement of another component. So, for example it is possible to place reagent vials for both ethanol and acetonitrile, in contrast to the prior art single-run cassettes that have either ethanol or acetonitrile rather than both, and the dual-run cassette described in WO2015071288 where only acetonitrile is available. Ethanol can be used in the conditioning of SPE columns, in the cleaning steps between first and second batches, and can be used as a radiostabilizer if desired. As described in Example 1 below for [$^{18}$F]FDG synthesis, reversed-phase purification column of an exemplary system of the present invention can be rinsed between runs with ethanol and water independently of the alumina column such that there is a negligible amount of Kryptofix™ 222 in the both batches of [$^{18}$F]labelled compound, thereby providing an advantage over WO2015071288 where the second batch has a higher concentration. Acetonitrile is the ideal drying solvent to remove water effectively during evaporation processes and can also be used in conditioning of SPE columns Having both solvents available is advantageous therefore in terms of flexibility of the process used.

Also, the configuration of the present invention allows an enriched water recycling pathway only on the left side of the cassette for both FDG batch (FIG. 5) (avoid contamination of the manifold with water and of the enriched water with residual organic solvents) with only six positions (the activity inlet, position 1 with the connection of enriched water vial, position 4 for the QMA 1, position 5 for tubing of QMA 2, position 7 for tubing of QMA 1 and position 8 for the QMA 2) on the cassette engaged.

The present invention therefore provides clear advantages over the methods and systems of the prior art.

DETAILED DESCRIPTION OF THE PREFERRED EMBODIMENTS

To more clearly and concisely describe and point out the subject matter of the claimed invention, definitions are provided in the description hereinbelow for specific terms used throughout the present specification and claims. Any exemplification of specific terms herein should be considered as non-limiting examples.

The term "length of tubing" refers to a suitable length of tubing formed from a flexible polymeric material. Non-limiting examples of suitable such flexible polymeric materials include silicone, PVC, FEP and PEEK.

The terms "first end" and "second end" are used in the context of the two ends of a component of the invention. In certain embodiments, the first end is proximal to the common pathway and the second end is distal to the common pathway.

The term "fluidly connected" used herein means that it is possible for fluid to pass to and/or from one feature of the invention to another feature of the invention, e.g. by use of a suitable valve. In one embodiment of the invention a suitable valve is a 3-way valve having three ports and means to put any two of the three associated ports in fluid communication with each other while fluidly isolating the third port. In another embodiment of the invention a suitable valve is a stopcock valve comprising a rotatable stopcock.

The term "common pathway" is to be understood to be a fluid pathway to which the other components of the system or of single-use cassette of the present invention are selectively fluidly connected. In one embodiment, the common pathway is a linear fluid pathway. In one embodiment, the common pathway is made from a rigid pharmaceutical grade polymeric material that is resistant to radiation. Non-limiting examples of suitable such rigid polymeric materials include polypropylene, polyethylene, polysulfone and Ultem®. In one embodiment, said common pathway is made from polypropylene or polyethylene. In one embodiment, said common pathway is linear.

In the context of the present invention the term "two consecutive batches" refers to the production of two separate first and second batches of $^{18}$F-fluoride or of an $^{18}$F-labelled compound on the same cassette, the second batch being produced only after production of the first batch has been completed.

By the term "cassette" is meant a piece of apparatus designed to fit removably and interchangeably onto an automated synthesis apparatus, in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. In one embodiment each valve is a 3-way valve. In one embodiment each valve is a stopcock valve comprising a rotatable stopcock. Each valve has a male-female joint which interfaces with a corresponding moving arm of the automated synthesis apparatus. External rotation of the arm thus controls the opening or closing of the valve when the cassette is attached to the automated synthesis apparatus. Additional moving parts of the automated synthesis apparatus are designed to clip onto syringe plunger tips, and thus raise or depress syringe barrels. The cassette is versatile, typically having several positions where reagents can be attached, and several suitable for attachment of syringe vials of reagents or chromatography columns. The cassette always comprises a reaction vessel, generally configured such that 3 or more ports of the cassette are connected thereto to permit transfer of reagents or solvents from various ports on the cassette. Cassettes need to be designed to be suitable for radiopharmaceutical manufacture and are therefore manufactured from materials which are of pharmaceutical grade as well as resistant to radiolysis. In one embodiment of the present invention the single-use cassette is a FASTlab™ cassette, i.e. one which is suitable for use with a FASTlab™ automated synthesis apparatus.

The term "single-use" as used in the context of a cassette of the present invention means that the cassette is intended to be used once prior to disposal for the production of two batches of an $^{18}$F-labelled compound.

By the term "automated synthesis apparatus" is meant an automated module based on the principle of unit operations as described by Satyamurthy et al (1999 Clin Positr Imag; 2(5): 233-253). The term 'unit operations" means that complex processes are reduced to a series of simple operations or reactions, which can be applied to a range of materials. Such automated synthesis apparatuses are preferred for the method of the present invention especially when a radiopharmaceutical composition is desired. They are commercially available from a range of suppliers (Satyamurthy et al, above), including: GE Healthcare; CTI Inc; Ion Beam Applications S.A. (Chemin du Cyclotron 3, B-1348 Louvain-La-Neuve, Belgium); Raytest (Germany) and Bioscan (USA). Automated synthesis apparatuses are designed to be employed in a suitably configured radioactive work cell, or "hot cell", which provides suitable radiation shielding to protect the operator from potential radiation dose, as well as ventilation to remove chemical and/or radioactive vapours. Using a cassette the automated synthesis apparatus has the flexibility to make a variety of different radiopharmaceuticals with minimal risk of cross-contamination, by simply changing the cassette. This approach also has the advantages of simplified set-up hence reduced risk of operator error, improved GMP (good manufacturing practice) compliance, multi-tracer capability, rapid change between production runs, pre-run automated diagnostic checking of the cassette and reagents, automated barcode cross-check of chemical reagents vs the synthesis to be carried out, reagent traceability, single-use and hence no risk of cross-contamination, tamper and abuse resistance.

A "reaction vessel" in the context of the present invention is a container selectively fluidly connected to the common pathway of the single-use cassette of the invention in order that the reactants and reagents required for the synthesis can be sent to the reaction vessel and the product(s) removed in an appropriate order. The reaction vessel has an internal volume suitable for containing the reactants and reagents and is made from pharmaceutical grade materials resistant to radiation.

The term "reagent vial" is taken to mean a vial containing one of the reagents for use in the production of the $^{18}$F-labelled compound. A typical reagent vial is made from a rigid pharmaceutical grade polymer resistant to radiation. Suitable reagents contained in said reagent vials include ethanol, acetonitrile, deprotecting agent and buffer. In one embodiment said deprotecting agent is selected from HCl, NaOH and $H_3PO_4$. In one embodiment said deprotecting agent is NaOH. In one embodiment said buffer is based on a weak acid, for example selected from citrate, phosphate, acetate and ascorbate. For example where the $^{18}$F-labelled compound of the present invention is [$^{18}$F]FDG, the single-use cassette comprises a reagent vial containing ethanol, one containing acetonitrile, another containing NaOH and another containing a buffer based on a weak acid selected from citrate or phosphate.

The term "means for cleaning" refers to a source of reagent selectively fluidly connected to the component to be cleaned. The selective fluid connection suitably comprises a valve and length of flexible tubing. Suitable reagents for cleaning include ethanol and acetonitrile, aqueous solutions thereof, and water. The term "cleaning" in the context of the present invention refers to the process of passing a suitable amount of one or more reagents through a component to be cleaned in order to render it suitable for use in preparation of the second batch of $^{18}$F-labelled compound.

The term "sufficient" as used in the context of eluent and precursor compound for the two consecutive batches means a suitable amount thereof to ensure that two batches of the $^{18}$F-labelled compound can be obtained. Generally this amount is a little more than the exact amount required.

The "product collection vial" is suitably a clinical grade syringe or a container which is provided with a seal which is suitable for single or multiple puncturing with a hypodermic needle (e.g. a crimped-on septum seal closure) whilst maintaining sterile integrity. Suitable containers comprise a sealed vessel which permits maintenance of sterile integrity and/or radioactive safety, whilst permitting addition and withdrawal of solutions by syringe. A preferred such container is a septum-sealed vial, wherein the gas-tight closure is crimped on with an overseal (typically of aluminium). Such containers have the additional advantage that the closure can withstand vacuum if desired e.g. to change the headspace gas or degas solutions.

The term "buffer" as used in the present invention refers to a solution comprising a weak acid that functions to prevent a rapid change in pH when acids or bases are added to the solution. In one embodiment said weak acid is selected from citrate, phosphate, acetate and ascorbate. For example where the $^{18}$F-labelled compound of the present invention is [$^{18}$F]FDG, the single-use cassette comprises a reagent vial containing ethanol, one containing acetonitrile, another containing NaOH and another containing a buffer based on a weak acid selected from citrate or phosphate.

The term "solid phase extraction (SPE)" refers to a sample preparation process by which compounds in a solution are separated from each other based on their respective affinities for a solid (the "solid phase", or "stationary phase") through which the sample is passed and the solvent (the "mobile phase" or "liquid phase") in which they are dissolved. The result is that a compound of interest is either retained on the solid phase or in the mobile phase. The portion that passes through the solid phase is collected or discarded, depending on whether it contains the compound of interest. If the portion retained on the stationary phase includes the compound of interest, it can then be removed from the stationary phase for collection in an additional step, in which the stationary phase is rinsed with another solution known as an "eluent". For the present invention SPE is suitably carried out using an "SPE column" (also often referred to as an "SPE cartridge"), which is readily available commercially and is typically in the form of a syringe-shaped column packed with solid phase. Most known solid phases are based on silica that has been bonded to a specific functional group, e.g. hydrocarbon chains of variable length (suitable for reversed-phase SPE), quaternary ammonium or amino groups (suitable for anion exchange), and sulfonic acid or carboxyl groups (suitable for cation exchange).

"Reversed-phase SPE" makes use of a nonpolar modified solid phase and a polar mobile phase. Compounds are retained by hydrophobic interactions and eluted using a non-polar elution solvent to disrupt the forces that bind the compound to the solid phase. Non-limiting examples of reversed-phase SPE columns include those wherein the chemistry is selected from octadecyl(C18 or tC18), octyl (C8), cyano (CN), diol, hydrophilic modified styrene polymer (HLB e.g. Oasis® HLB from Waters), polymeric poly(divinylbenzene-vinylpyrrolidone) (e.g. Porapak® RDX resin available from Waters), and $NH_2SPE$ columns. The term "chemistry" in the context of SPE columns refers to the surface groups that interact with the solution being purified and typically an SPE column is referred to by its chemistry, e.g. a SPE column with C18 chemistry is referred to as a "C18 column" In one embodiment of the present invention the chemistry of the reversed-phase SPE column is a tC18 column or a HLB column. In another embodiment of the present invention the reversed-phase SPE column is a tC18 column. In some embodiments of the present invention the tC18 column is an environmental tC18 column, sometimes referred to as a long tC18 column or a tC18 plus column.

The term "normal-phase" used in connection with SPE and SPE columns refers to SPE separation that makes use of a polar modified solid phase and a non-polar mobile phase. Compounds are retained by hydrophilic interactions and eluted using a solvent that is more polar than the original mobile phase to disrupt the binding mechanism. Non-limiting examples of normal-phase SPE columns include alumina, diol and silica SPE columns.

The term "anion exchange" used in connection with SPE and SPE columns refers to SPE separation that utilises electrostatic attraction of charged group on compound to a charged group on the sorbent's surface and can be used for compounds that are charged in solution. The primary retention mechanism of the compound is based mainly on the electrostatic attraction of the charged functional group on the compound to the charged group that is bonded to the silica surface. A solution having a pH that neutralizes either the compound's functional group or the functional group on the sorbent surface is used to elute the compound of interest. A non-limiting example of an anion exchange SPE column is a quaternary ammonium anion exchange (QMA) SPE column.

The term "eluting" refers to passing a solution through an SPE column with the aim to release a compound or compounds of interest that has or have been bound to the solid phase. The terms "eluent" and "eluting" are also specifically used in connection with the present invention to refer to the eluent used to elute $^{18}F$-fluoride trapped on the anion exchange column. $^{18}F$-fluoride suitable for use in the synthesis of an $^{18}F$-labelled compound is normally obtained as an aqueous solution from the nuclear reaction $^{18}O(p,n)^{18}F$. In order to increase the reactivity of $^{18}F$-fluoride and to reduce or minimise hydroxylated by-products resulting from the presence of water, water is typically removed from $^{18}F$-fluoride prior to the reaction, and fluorination reactions are carried out using anhydrous reaction solvents (Aigbirhio et al 1995 J Fluor Chem; 70: 279-87). A further step that is used to improve the reactivity of $^{18}F$-fluoride for radiofluorination reactions is to add a cationic counterion prior to the removal of water. This cationic counterion is dissolved in an organic-aqueous solution and this solution is used as an eluent for eluting $^{18}F$-fluoride from an anion exchange column on which the $^{18}F$-fluoride has been trapped. Suitably, the counterion should possess sufficient solubility within the anhydrous reaction solvent to maintain the solubility of the $^{18}F$-fluoride. Therefore, counterions that are typically used include large but soft metal ions such as rubidium or caesium, potassium complexed with a cryptand such as Kryptofix™ 222, or tetraalkylammonium salts, wherein potassium complexed with a cryptand such as Kryptofix™ 222, or tetraalkylammonium salts are preferred. The term Kryptofix™ 222 (or K222) refers herein to a commercially-available preparation of the compound 4,7,13,16,21,24-Hexaoxa-1,10-diazabicyclo[8.8.8]hexacosane.

An "$^{18}F$-labelled compound" is a chemical compound that comprises an $^{18}F$ atom. Non-limiting examples of $^{18}F$-labelled compounds include [$^{18}F$]fluorodeoxyglucose ([$^{18}F$]FDG), [$^{18}F$]Fluoromisonidazole ([$^{18}F$]FMISO), [$^{18}F$]fluorothymidine ([$^{18}F$]FLT), [$^{18}F$]Fluoroazomycin arabinofuranoside ([$^{18}F$]FAZA), [$^{18}F$]Fluoroethyl-choline ([$^{18}F$]FECH), [$^{18}F$]fluorocyclobutane-1-carboxylic acid ([$^{18}F$]FACBC), [$^{18}F$]-flumanezil ([$^{18}F$]FMZ), [$^{18}F$]-tyrosine, [$^{18}F$]-altanaserine, 4-[$^{18}F$]-fluoro-3-iodobenzyl guanidine ([$^{18}F$]-FIBG), meta-[$^{18}F$]fluorobenzylguanidine ([$^{18}F$]-mFBG) and [$^{18}F$]-5-fluorouracil. In one embodiment of the present invention the $^{18}F$-labelled compound is selected from [$^{18}F$]FDG, [$^{18}F$]FMISO, [$^{18}F$]FLT and [$^{18}F$]FACBC. In another embodiment of the present invention the $^{18}F$-labelled compound is [$^{18}F$]FDG.

A "precursor compound" is to be understood herein as a non-radioactive derivative of a radiolabelled compound, designed so that chemical reaction with a convenient chemical form of the detectable label occurs site-specifically in the minimum number of steps (ideally a single step) to give the desired radiolabelled compound. Such precursor compounds are synthetic and can conveniently be obtained in good chemical purity. A number of precursor compounds are well known to be suitable for the synthesis of $^{18}F$-labelled compounds, as taught for example in Chapter 7 of "Handbook of Radiopharmaceuticals: Radiochemistry and Applications" (2003 John Wiley & Sons Ltd., Wench & Redvanly, Eds.).

The term "protecting group" refers to a group which inhibits or suppresses undesirable chemical reactions, but which is designed to be sufficiently reactive that it may be cleaved from the functional group in question (also called "deprotection") to obtain the desired product under mild enough conditions that do not modify the rest of the molecule. Protecting groups are well known to those skilled in the art and are described in 'Protective Groups in Organic Synthesis', Theorodora W. Greene and Peter G. M. Wuts, (Fourth Edition, John Wiley & Sons, 2007). In one embodiment of the present invention deprotection is carried out using an SPE column for deprotection. An "SPE column for deprotection" is an SPE column having a solid phase on which a precursor compound having protecting groups is retained following the $^{18}F$-labelling reaction in order to remove the protecting groups and obtain the desired $^{18}F$-labelled compound. In one embodiment the SPE column for deprotection is a reversed-phase SPE column as defined herein. Deprotection is carried out using a suitable "deprotecting agent", non-limiting examples of which include HCl, NaOH and $H_3PO_4$. In one embodiment said deprotecting agent is NaOH.

The term "labelling" used in connection with labelling a precursor compound with an aliquot of [$^{18}F$]fluoride is taken to mean the reaction that takes place such that $^{18}F$ becomes covalently bound to said precursor compound. Typically said labelling is carried out by adding reactive [$^{18}F$]fluoride to a solution of the precursor compound in a reaction vessel and elevating the temperature, e.g. to around 100-150° C. for a short duration of around 2-10 minutes.

The "[$^{18}$F]-labelled product" referred to in the method for the synthesis of two consecutive batches of an [$^{18}$F]-labelled compound of the present invention is the solution obtained directly following labelling of a precursor compound with $^{18}$F, i.e. before the optional post-labelling deprotection and/or purification steps.

The term "purification" as used herein may be taken to mean a process to obtain substantially pure $^{18}$F-labelled compound. The term "substantially" refers to the complete or nearly complete extent or degree of an action, characteristic, property, state, structure, item, or result. The term "substantially pure" can be taken to mean completely pure $^{18}$F-labelled compound, which would be ideal, but also $^{18}$F-labelled compound that is sufficiently pure to be suitable for use as a PET tracer. The term "suitable for use as a PET tracer" means that the substantially pure $^{18}$F-labelled compound is suitable for intravenous administration to a mammalian subject followed by PET imaging to obtain one or more clinically-useful images of the location and/or distribution of the $^{18}$F-labelled compound.

Figure 5:
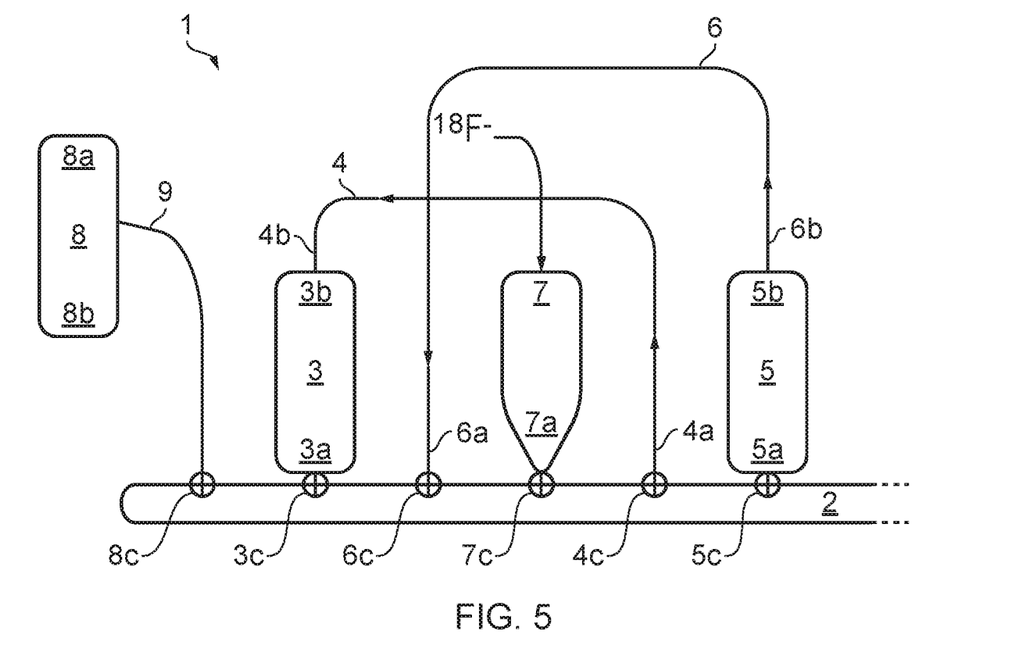
FIG. 5 illustrates an example of the system for trapping [$^{18}$F]fluoride and recovering [$^{18}$O]water of the present invention.

FIG. 5 is a schematic illustration of an exemplary system 1 of the present invention for trapping [$^{18}$F]fluoride and recovering [$^{18}$O]water. For a first batch of [$^{18}$F]fluoride, an aqueous solution from the nuclear reaction $^{18}$O(p,n)$^{18}$F produced on a cyclotron enters the system through vial 7. The valves 3c, 4, 7c and 8c are positioned to permit flow from the vial 7 through tubing 4, then QMA column 3, then tubing 9 and into the [$^{18}$O]water recovery vial 8. The [$^{18}$F]-fluoride trapped on the QMA is eluted into a reaction vessel with a suitable eluent as described hereinabove and used in the production of an [$^{18}$F]-labelled compound. A second batch of [$^{18}$F]fluoride is similarly produced but where the aqueous solution from the nuclear reaction $^{18}$O(p,n)$^{18}$F follows the pathway from vial 7 through QMA column 5, then tubing 6 and finally tubing 9 and the [$^{18}$O]-water recovery vial 8. This is advantageous over previous methods as fewer positions are required for the system, and the activity is contained within a smaller space. This is particularly advantageous in the context of a single-use FASTlab™ cassette, where there are a limited number of positions available, but is also generally advantageous for automated synthesis of [$^{18}$F]-labelled compounds where it is always desirable for equipment to be as compact as possible in order to occupy as little space in a hot cell as possible.

Figure 6:
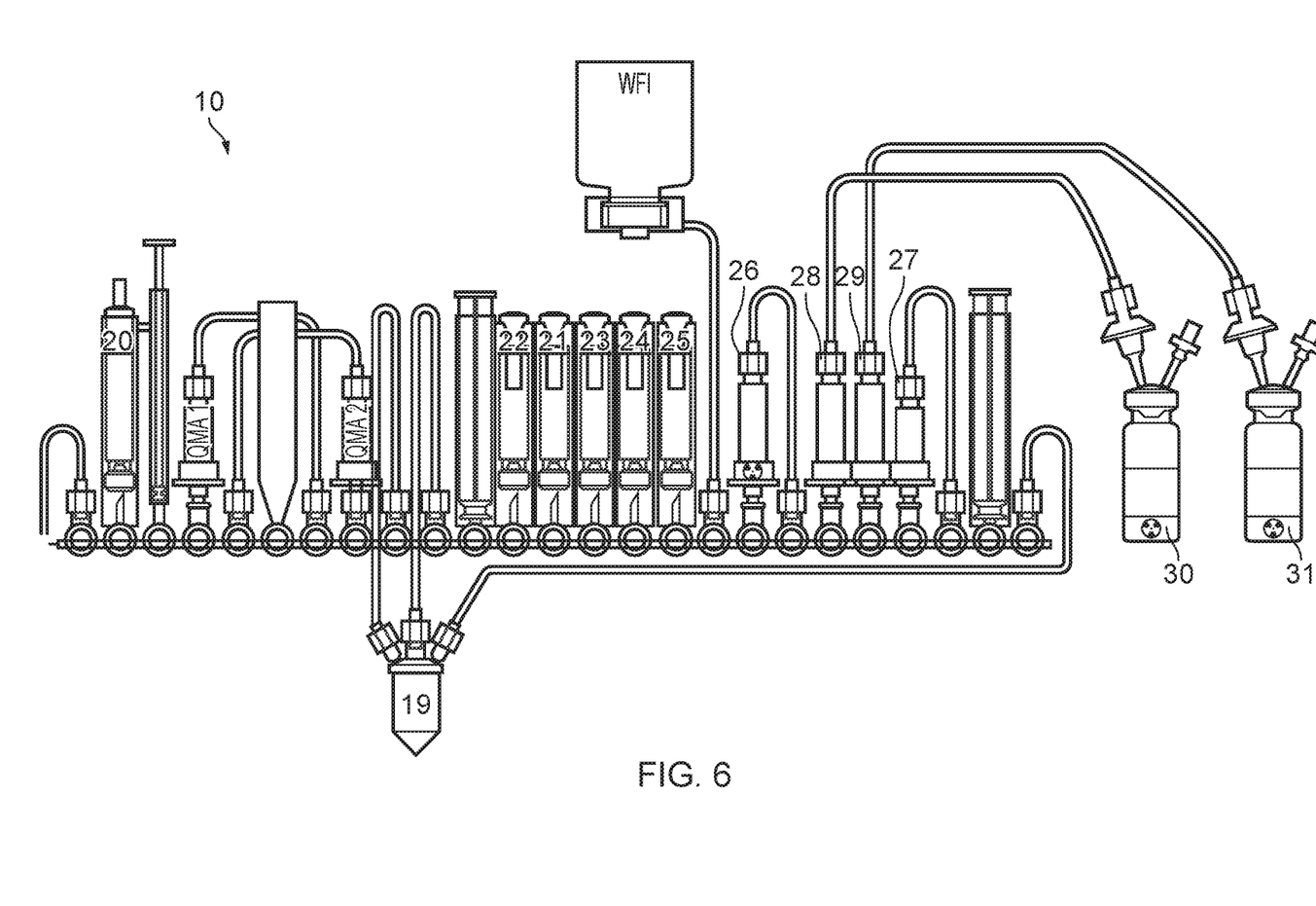
FIG. 6 illustrates an exemplary single-use cassette according to the present invention.
Figure 7:
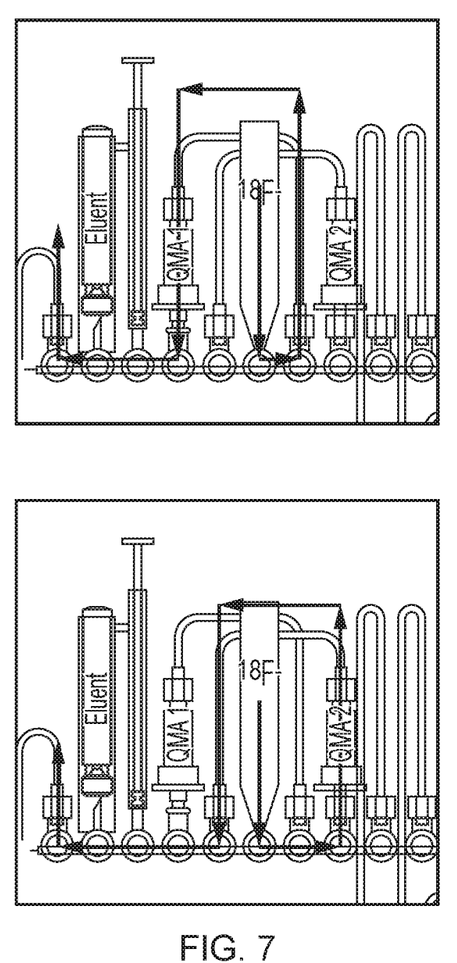
FIG. 7 illustrates an embodiment of the system of the present invention showing the enriched water recycling pathways for the first (top) and second (bottom) batches of [$^{18}$F]fluoride.

Use of the single-use cassette of FIG. 6 and the system of FIG. 7 is described in Example 1 below where it is demonstrated that two consecutive batches of [$^{18}$F]-FDG having similar chemical and radiochemical profiles can be obtained from one cassette. This is important for [$^{18}$F]-FDG and other [$^{18}$F]-labelled PET tracers where defined pharmacopoeial parameters need to be met.

Any commonly-present features and embodiments of the present invention are equally applicable across the various aspects of the present invention.

BRIEF DESCRIPTION OF THE EXAMPLES

Example 1 described the synthesis of two batches of [$^{18}$F]FDG on one FASTlab cassette According to an embodiment of the present invention.

LIST OF ABBREVIATIONS USED IN THE EXAMPLES

EtOH ethanol
[$^{18}$F]FDG $^{18}$F-fluorodeoxyglucose
[$^{18}$F]FDGc citrate-buffered $^{18}$F-fluorodeoxyglucose
[$^{18}$F]FTAG $^{18}$F-fluoro-tetraacetyl-glucose
IC ionic chromatography
ICP-MS inductively coupled plasma mass spectrometry
K222 4,7,13,16,21,24-Hexaoxa-1,10-diazabicyclo[8.8.8]hexacosane
KI potassium iodide
LB low bleed phase
mCi milli Curie
MeCN acetonitrile
ppm parts per million
QMA quaternary methylammonium
TLC thin layer chromatography

EXAMPLES

Example 1: Synthesis of Two Batches of [$^{18}$F]FDG on One FASTlab Cassette According to an Embodiment of the Present Invention The cassette configuration as illustrated in FIG. 5 was used in this Example.

(1) The tC18 environmental at position 18 was conditioned with 800 μL MeCN from the reagent vial at position 15 and the tC18 plus column at position 22 was conditioned with 1.5 mL EtOH from the reagent vial at position 12.

(2) [$^{18}$F]-fluoride was obtained from the bombardment of [$^{18}$O]—H$_2$O with a high-energy proton beam extracted from a cyclotron (Cyclotron Cyclone 18/9 from IBA) and transferred to the FASTlab cassette via the conical reservoir at position 6.

(3) [$^{18}$F]Fluoride was trapped on the QMA column at position 4 and separated from the enriched water which was collected in an external vial via a V7-V4-V1 pathway.

(4) Eluent was withdrawn in the syringe at position 3 and passed through the QMA column at position 4 to release [$^{18}$F]fluoride and send to the reaction vessel.

(5) Evaporation of the water from the reaction vessel was catalysed by adding around 100 μL of acetonitrile from the vial at position 15 at 120° C.

(6) Mannose triflate precursor from position 13 was withdrawn in the syringe at position 11 and transferred to the reaction vessel connected to positions 9, 10 and 25 where the labelling reaction was carried out 125° C. for 2 minutes.

(7) The resulting radiolabelling compound ($^{18}$F-fluoro-tetraacetyl-glucose, [$^{18}$F]FTAG) was trapped and so, separated from unreacted fluorides, on the lower side of the tC18 environmental column.

(8) Sodium hydroxide was passed through the column to convert the [$^{18}$F]FTAG to [$^{18}$F]FDG collected by the syringe at position 24.

(9) Neutralization of the resulting basic solution was carried out using hydrochloric acid contained in a citrate buffer.

(10) The product was purified by following this pathway: tC18 plus column-Alumina N found at position 20 directly connected to the first product collection vial.

(11) The tC18 environmental was washed with acetonitrile from position 15, the tC18 plus was washed with ethanol from position 12, and the reactor, purification columns and tubing were washed with water from the water bag connected as position 17 The tC18 environmental was rinsed with 1 mL of acetonitrile and 5 mL of water, the tC18 plus with 1 mL of ethanol and 4 mL of water.

(12) A second batch of [$^{18}$F]-fluoride from the cyclotron was transferred to the FASTlab cassette as in step (2).

(13) The [$^{18}$F]fluoride was trapped on a new QMA column found at position 8 and separated from the enriched water which is collected in an external vial via a pathway through positions 8-5-1.

(14) With [$^{18}$F]fluoride from the QMA at position 8, steps (4)-(9) were carried out as for the first batch.

(15) The second batch of [$^{18}$F]FDG was purified along the pathway: tC18 plus column at position 22-Alumina N found at position 21 directly connected to the second product collection vial.

The results below are obtained with this cassette configuration:

The GC column was a Macherey-Nagel OPTIMA 624 (6% cyanopropylphenyl-94% dimethylpolysiloxane), LB (=Low Bleed phase), 30 m (=length), 0.32 mm (=inner diameter), 1.8 μm (=film thickness).

The following parameters were used:
Mobile phase=helium (flow=5 mL/min)
Injection samples (injection volume=0.5 μL)
1. 1.6 mL water (=blank)
2. 1.6 mL standard solution (5000 ppm in EtOH; 273 ppm in MeCN)
3. 1.6 mL sample requiring analyses Gas flow to detector:—helium (=20 mL/min)

| Run ID | Sequence used | Yield (non-corrected %) | Starting Activity (mCi) | Residual activity on QMA (%) | Residual activity in enriched water vial (%) | K222 in the final product (ppm) | EtOH in the final product (ppm) |
|---|---|---|---|---|---|---|---|
| FLdualFDGc25F EB14-LA1 | GE_dualFDGc_PETCS018FL | 61.96 | 7.506 | 0.18 | 0.00 | 1 | 398 |
| FLdualFDGc25F EB14-LA2 | GE_dualFDGc_PETCS018FL | 70.90 | 7.479 | 0.21 | 0.00 | 1 | 2342 |
| FLdualFDGc26F EB14-LA1 | GE_dualFDGc_PETCS018FL | 69.27 | 6.756 | 0.08 | 0.09 | 1 | 494 |
| FLdualFDGc26F EB14-LA2 | GE_dualFDGc_PETCS018FL | 70.11 | 7.507 | 0.00 | 0.02 | 1 | 2185 |
| FLduoFDGc10A PR14-LA1 | GE_dualFDGc_PETCS003FL | 76.25 | 8.356 | 0.00 | 0.00 | 1 | 2778 |
| FLduoFDGc10A PR14-LA2 | GE_dualFDGc_PETCS003FL | 81.67 | 6.586 | 0.04 | 0.00 | 1 | 2766 |
| FLduoFDGc10A PR14-LB1 | GE_duoFDGc_PETCS003FL | 78.81 | 8.981 | 0.00 | 0.00 | 1 | 2824 |
| FLduoFDGc10A PR14-LB2 | GE_duoFDGc_PETCS003FL | 77.23 | 10.272 | 0.02 | 0.00 | 1 | 3094 |
| FLduoFDGc08M AY14-HA& | GE_duoFDGc_PETCS006FL | 74.84 | 5625 | NA | NA | 1 | 801 |
| FLduoFDGc09M AY14-HA2 | GE_duoFDGc_PETCS006FL | 75.43 | 5223 | 0.09 | 0.01 | 1 | 1614 |

Starting activity, final activity and residual activities were measured by a calibrated ionization chamber VEENSTRA (VIK-202).

To determine yield, the following yield Calculations were made:
if delta Tf=elapsed time after time at starting of the synthesis in min
if Af=final activity in mCi
cAf=corrected final activity in mCi regarding to starting of the synthesis in min=Af. Exp(ln(2)*(delta Tf/110)) where 110=half-life of [$^{18}$F]fluorine in minutes
if cAi=corrected starting activity in mCi regarding to starting of the synthesis in mCi
if delta Ts=duration of the synthesis
Corrected yield (CY)=(cAf/cAi)*100
Uncorrected yield (NCY)=CY*Exp(ln(2)*(–delta Ts/110))

The amount of Kryptofix 2.2.2 in the final product was determined by spotting the sample on a TLC plate which is impregnated by a revealing solution of iodoplatinate (0.5 g of Chloroplatinic acid hexa-hydrated: $H_2PtCl_6.6H_2O$ (!highly hygroscopic!), 9 g of potassium iodide: KI, 200 mL of distilled water) and comparing this with standard solutions of Kryptofix 2.2.2 (1, 5, 10, 50 and 100 ppm). Colour intensity of the obtained stains is proportional to the amount of Kryptofix 2.2.2 present in the solution.

The amount of ethanol in the final product was verified by injecting the sample into a chromatography system called gas chromatography (VARIAN CP-3800, including autosampler, column inlet, column oven and flame ionization detector).

hydrogen (=35 mL/min)
compressed air (=360 mL/min)
Injector temperature=200° C.
Column oven temperature=temperature ramp from 50° C. to 220° C.
Detector temperature=250° C.
Acquisition time=15 minutes

The invention claimed is:

1. A cassette system for trapping [$^{18}$F]fluoride and recovering [$^{18}$O]water, the cassette system comprising:
(i) a first anion exchange column, the first anion exchange column having a first end and a second end;
(ii) a first length of tubing fluidly connected at its second end to the second end of said first anion exchange column;
(iii) a second anion exchange column, the second anion exchange column having a first end and a second end;
(iv) a second length of tubing fluidly connected at its second end to the second end of said second anion exchange column;
(v) a [$^{18}$F]fluoride inlet; and,
(vi) a [$^{18}$O]water recovery vial;
wherein the first end of the first anion exchange column and the first end of the second anion exchange column are fluidly connected to a common pathway within the cassette via a valve having three ports and means to put any two of the three associated ports in fluid communication with each other while fluidly isolating the third port wherein said first end of said first length of tubing is fluidly connected to said common pathway within the cassette at a point in between said second anion exchange column and said [$^{18}$F]fluoride inlet; and said first end of said second length of tubing is fluidly connected to said common pathway within the cassette at a point in between said first anion exchange column and said [$^{18}$F]fluoride inlet.

2. The system of claim 1, wherein said common pathway is linear.

3. The system of claim 1 wherein said common pathway is formed from a rigid polymeric material.

4. The system of claim 1, wherein each of said 3-way valves associated with said anion exchange columns, said lengths of tubing, and said [$^{18}$O]water recovery vial has a female luer connector projecting up therefrom.

5. The system of claim 1, wherein said 3-way valve associated with said [$^{18}$F]fluoride inlet has an elongate open vial housing upstanding therefrom and supports an upstanding cannula therein.

6. The system of claim 1, wherein each of said valves is a stopcock valve comprising a rotatable stopcock.

7. The system of claim 1, wherein each of said anion exchange columns is a quaternary methylammonium (QMA) solid-phase extraction (SPE) column.

8. The system of claim 1, wherein each of said lengths of tubing is formed from a flexible polymeric material.

9. The system of claim 1, wherein said [$^{18}$F]fluoride inlet comprises a [$^{18}$F]fluoride inlet reservoir.

10. A single-use cassette for the production of two consecutive batches of an [$^{18}$F]-labelled radiotracer comprising the system for trapping [$^{18}$F]fluoride and recovering[$^{18}$O] water of claim 1, further comprising:
(a) a reaction vessel and means for cleaning said reaction vessel;
(b) an eluent vial containing sufficient eluent for said two consecutive batches;
(c) a precursor vial containing sufficient precursor compound for said two consecutive batches;
(d) two reagent vials each containing a particular reagent in sufficient quantity for said two consecutive batches;
(e) first and second reversed-phase SPE columns and respective means for cleaning said SPE columns; and
(f) first and second normal-phase SPE columns, each fluidly connected to a respective product collection vial wherein the reaction vessel, the eluent vial, the precursor vial, the two reagent vials, the reversed-phase SPE columns, and the normal-phase SPE columns are connected to the common pathway.

11. The cassette of claim 10, wherein said means for cleaning said reaction vessel comprises a source of sterile water fluidly connected to said reaction vessel.

12. The cassette of claim 10, wherein said eluent comprises a cationic counterion dissolved in an organic-aqueous solution.

13. The cassette of claim 10, wherein said cationic counterion is selected from rubidium, caesium, potassium complexed with a cryptand and a tetraalkylammonium salt.

14. The cassette of claim 10, wherein said reagent vials comprise a vial containing ethanol, a vial containing acetonitrile, a vial containing a deprotecting agent and a vial containing buffer.

15. The cassette of claim 10, wherein the chemistry of said reversed-phase SPE column is selected from octadecyl (C18 or tC18), octyl (C8), cyano (CN), diol, hydrophilic modified styrene polymer (HLB), polymeric poly(divinylbenzene-vinylpyrrolidone) and NH2.

16. The cassette of claim 10, wherein said first reversed-phase SPE column is selected from a tC18 and a HLB SPE column.

17. The cassette of claim 10, wherein said first reversed-phase SPE column is a tC18 column.

18. The cassette of claim 10, wherein said second reversed-phase column is a tC18 column.

19. The cassette of claim 10, wherein each of said first and second normal-phase SPE columns is an alumina SPE column.

20. A method for trapping [$^{18}$F]fluoride and recovering [$^{18}$O]water for the synthesis of two consecutive batches of [$^{18}$F]-fluoride on a single cassette, the method comprising the following steps in sequence:
(I) providing a system of claim 1;
(II) setting the valves to create a first flowpath from the [$^{18}$F]fluoride inlet to the first length of tubing to the first anion exchange column and to the [$^{18}$O]water recovery vial wherein the remaining valves are closed;
(III) sending a first aliquot of an aqueous solution obtained from the nuclear reaction $^{18}$O(p,n)$^{18}$F through said first flowpath;
(IV) setting the valves to create a second flowpath from the [$^{18}$F]fluoride inlet to the second length of tubing to the second anion exchange column and to the [$^{18}$O] water recovery vial wherein the remaining valves are closed; and
(V) sending a second aliquot of an aqueous solution obtained from the nuclear reaction $^{18}$O(p,n)$^{18}$F through said second flowpath.

* * * * *